Figure 1:
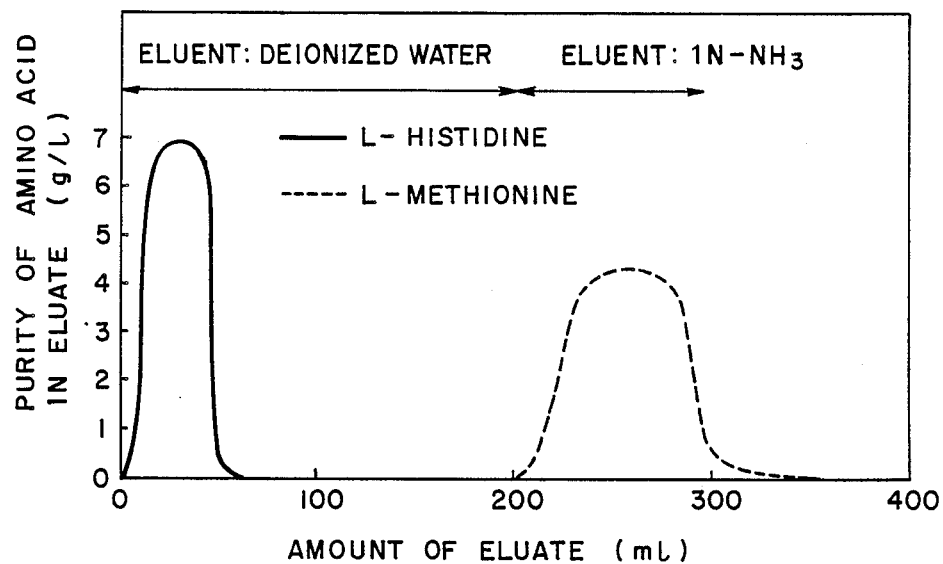
Figure 2:
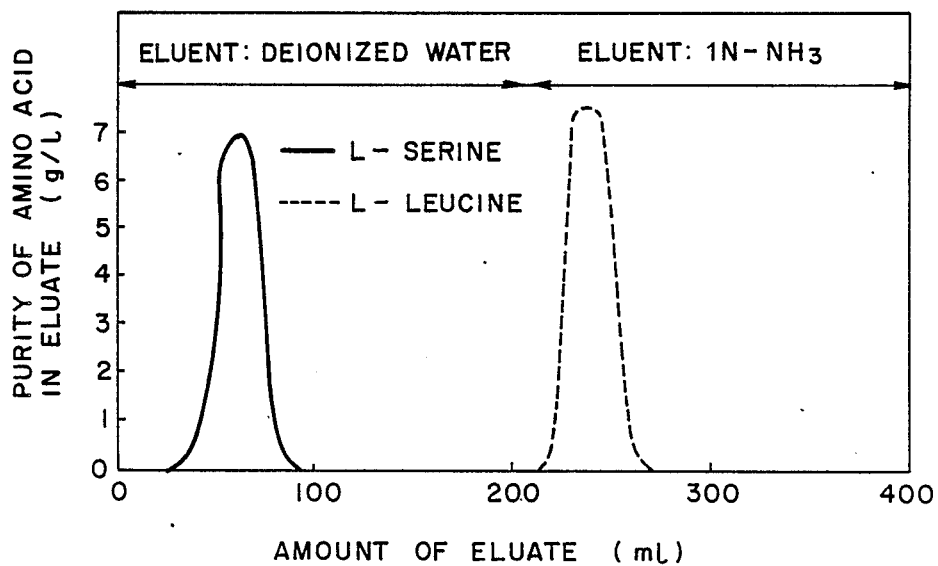
Figure 3:
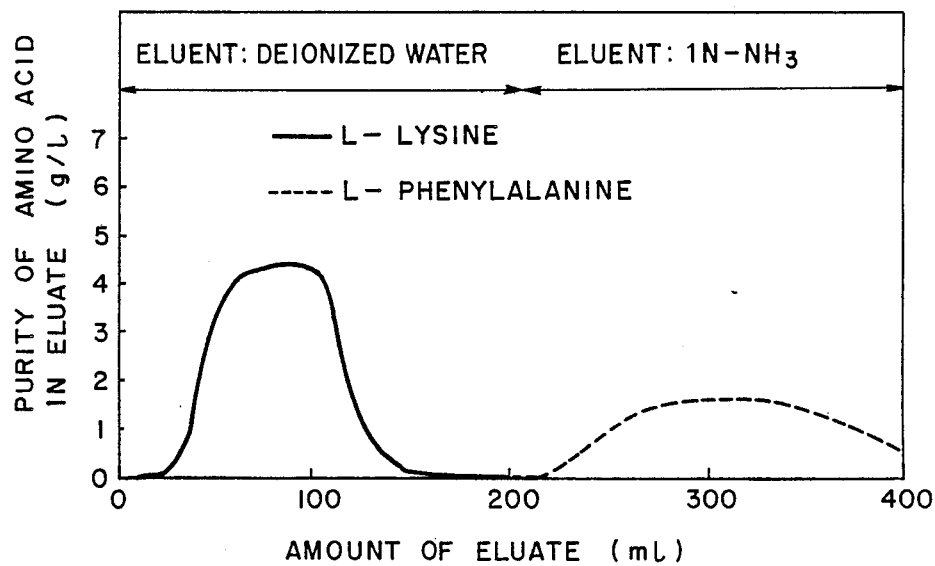
Figure 4:
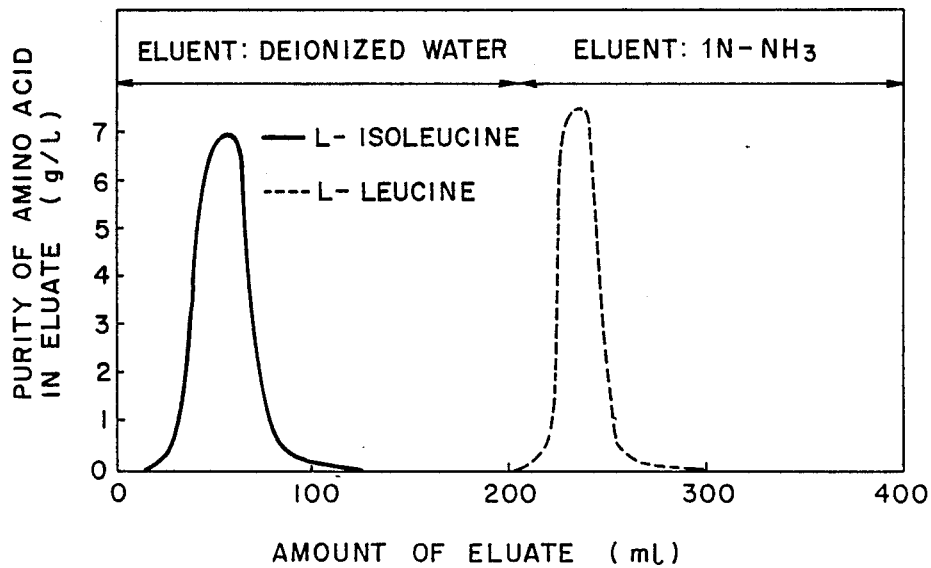

United States Patent [19]

Matsuda et al.

[11] Patent Number: 4,927,541
[45] Date of Patent: May 22, 1990

[54] PROCESS FOR REFINING AMINO ACIDS

[75] Inventors: Masaaki Matsuda; Yuji Yoshida, both of Osaka, Japan

[73] Assignee: Sumitomo Chemical Company, Limited, Osaka, Japan

[21] Appl. No.: 332,172

[22] Filed: Apr. 3, 1989

[30] Foreign Application Priority Data

Apr. 8, 1988 [JP] Japan ................................ 63-87551

[51] Int. Cl.⁵ ............................................ B01D 15/08
[52] U.S. Cl. .................................. 210/656; 210/672; 530/413
[58] Field of Search ...................... 210/635, 656, 672; 530/413, 416, 417

[56] References Cited

U.S. PATENT DOCUMENTS 4,290,893  9/1981  Hare et al. .......................... 210/656

OTHER PUBLICATIONS

FINE CHEMICALS, Mar. 15, 1982, p. 10.

Primary Examiner—Ivars Cintins
Attorney, Agent, or Firm—Cushman, Darby & Cushman

[57] ABSTRACT

Amino acid each is separated and refined by bringing aqueous solution containing various amino acids into contact with chelate resins having aminocarboxylic acid groups or aminophosphonic acid groups and having metal ions coordinated, until amino acids are absorbed on the resins, and then eluting the acids.

6 Claims, 2 Drawing Sheets

PROCESS FOR REFINING AMINO ACIDS

BACKGROUND OF THE INVENTION

The present invention relates to a process for refining amino acids. More particularly, it relates to a process for refining amino acids by using chelate resins having chelate groups which coordinate metal ions.

Amino acids are widely used for foods, feed, medicines, cosmetics and other commercial products.

Amino acids are produced by fermentation processes, synthesis processes or extraction processes. Crude amino acids produced by these processes are usually refined in order to obtain the desired amino acids for commercial uses by separating from raw materials and by-products, such as undesired amino acids contaminated in the crude amino acids.

The separation of the desired amino acids from the raw material or the by-products is generally conducted by a crystallization method utilizing the difference of solubilities. The crystallization method is usually conducted in aqueous solution, because solubility of amino acids in organic solvents usually used is small. However, repetition of the crystallization is needed in order to obtain the refined amino acid of high purity, since solubility of an amino acid is often very close to that of the other amino acid in aqueous solution. This makes the operation complicated. Furthermore, the crystallization method is hardly applied to for separation of, for example, leucine from isoleucine, structure isomer thereof. The third components such as $\beta$-naphthalene sulfonic acid or 2-bromo-5-toluene sulfonic acid are added to the amino acids to form salts of the respective amino acids, and then one salt is separated from another salt by taking advantage of the difference of respective solubilities (Fine Chemical, Mar. 15, 1982, page 10). Accordingly, lots of time and many equipments and apparatuses are needed for refining amino acids. Equipment cost and running cost are very large.

Under the circumstances, the inventors have made extensive study to find an efficient process for refining amino acids. As the result, the inventors succeeded in establishment of the present invention.

SUMMARY OF THE INVENTION

In accordance with the present invention, a refining process of an amino acid is provided which comprises bringing aqueous solution of amino acids into contact with chelate resins having aminocarboxylic acid groups or aminophosphonic acid groups which coordinate metal ions and then eluting the amino acid.

The chelate resins usuable in the present invention are obtained by any of known methods. Any base resins and shapes may be used.

I. Examples of chelate resins having aminocarboxylic acid groups.

(1) Resins which are prepared by allowing amino resins or polyamino resins having one or more primary and/or secondary amino groups to react with a halogenated alkyl carboxylic acid compound such as monochloroacetic acid, monobromoacetic acid, monochloropropionic acid, monobromopropionic acid, alkali metal salts thereof or alkaline earch metal salts thereof.

The amino resins mentioned above are prepared by allowing ammonia, methylamine or ethylamine to react with polymers having amino-reactive groups such as nitrile group, a chloromethyl group, a sulfonylchloride group, a carbonylchloride group, an isocyanate group, an epoxy group, aldehyde group and halogen atom (chlorine, bromine and iodine).

The polyamino resins mentioned above are prepared by allowing polyamines such as ethylenediamine, trimethylenediamine, tetramethylenediamine, pentamethylenediamine, hexamethylenediamine, octamethylenediamine, nonamethylenediamine, diethylenetriamine, triethylenetetramine, tetraethylenepentamine, hydrazine or guanidine to react with the above mentioned polymer having amino-reactive groups.

(2) Resins which are prepared by allowing the above mentioned amino resins or polyamino resins to react with acrylic acid, methacrylic acid, acetylene dicarboxylic acid, maleic acid, alkali metal salts thereof, alkaline earch metal salts thereof, methyl or ethyl esters thereof, or the like (hereinafter referred to as "acrylic acid compound"). When esters are employed, hydrolysis of the product is necessary.

(3) Resins which are prepared by allowing the above mentioned polymers having the amino-reactive groups to react with an amino acid such as glycine, alanine, iminodiacetic acid, iminodipropionic acid, ethylenediamine diacetic acid, ethylenediamine triacetic acid or the like.

(4) Commercially available chelate resins such as "Sumichelate" MC-30, MC-75, MC-77, MC-78 (Trademarks for chelate resins manufactured by Sumitomo Chemical Co.), "Duolite" C-466 (manufactured by Duolite International Co.), "Diaion" CR-10 (manufactured by Mitsubishi Chemical Co.) and "Unicelex" OR-10, OR-20, OR-30, OR-40, OR-50 (manufactured by Unitika, Ltd.).

II. Examples of the chelate resins having aminophosphonic acid groups.

(1) Resins which are prepared by allowing amino resins or polyamino resins having one or more primary and/or secondary amino groups to react with alkyl phosphonation agents such as chloromethylphosphonic acid, chloroethylphosphonic acid or the like.

(2) Resins which are prepared by allowing the amino resins or polyamino resins to react with methylation agents such as formaldehyde and trioxymethylene, and phosphonation agents such as phosphorus trichloride, phosphorus acid, hypophosphite, methylphosphite, ethylphosphite in the presence of acid catalysts such as hydrochloric acid and sulfuric acid.

(3) Commercially available chelate resins such as "Sumichelate" MC-95 (manufactured by Sumitomo Chemical Co.), "Duolite" C-467 (manufactured by Duolite International) and "Unicelex" UR-3300 (manufactured by Unitika, Ltd.).

Among the resins above, preferable are so called polyalkylene polyaminocarboxylic acid resins or polyalkylene polyaminophosphonic acid resins in which the backbone polymers are connected with polyalkylene polyamino groups and the groups are further connected with carboxylic acid groups or phosphonic acid groups. The resins are prepared by allowing polyamino acid to react with halogenated alkyl carboxylic acid compounds, acrylic acid compounds, amino acid compounds, alkylphosphonation agents or alkylenation agents and phosphonation agents. Little leakage of metal ions coordinated with the chelate groups and little contamination of refined amino acid therewith facilitates the efficiency of separation. Particularly preferred is chelate resins having polyalkylene polyaminocarboxylic acid groups or polyalkylene polyphosphonic acid groups connected with acrylic base polymers, from a view point of separation efficiency.

Any metal ions which coordinate with the chelate groups are used as long as the chelate groups adsorb the amino acid to be refined, but preferably transition metal ions. Particularly, iron, cobalt, nickel, copper or zinc ions, i.e., ions of elements belonging to the fourth period of the Mendelejeff's periodic table, are preferable, because these metals are not expensive and the metal ions, if leaked and contaminated the refined amino acids, are removed easily.

Coordination of the metal ions onto the chelate groups of the chelate resins are effected by passing aqueous solution of the metal ions through a column in which the chelate resins are packed. Alternatively, the chelate resins are dipped in aqueous solution of the metal ions and then stirred.

An amount of the metal ions coordinated on the chelate groups has no special limitation, but usually it is not less than about 0.1 g atom per Kg resin up to saturation. If the amount is smaller than the above, refining efficiency decreases.

Conditions under which aqueous solution of the metal ions are brought into contact with the chelate resins are determined by conducting preliminary experiments, because they vary depending on varieties of the metal ions and chelate resins to be used, concentration of the metal ions in the aqueous solution, amount of the chelate resins, temperature, etc. Usually, 1 to 100 l of aqueous solution containing 0.01 to 0.5 mol/l of metal salts of a mineral acid or an amine complex salt of a metal is brought into contact with 1 Kg of chelate resin for 0.1 to 24 hours.

The chelate resins coordinating metal ions obtained by above mentioned method, with or without being washed with water, are brought into contact with aqueous solution of the amino acid to be refined. Any aqueous amino acid solution is used as long as affinities of the amino acids and impurities in the solution with the chelate groups in the resin which coordinate metal ion are different from each other. Examples of the amino acids are methionine, cystine, cystein, tyrosine, valine, phenylalanine, alanine, tryptophan, proline, serine, lysine, aminobutyric acid, leucine, isoleucine, etc. Examples of the impurities are raw materials for synthesis of amino acids such as anthranilic acid, 2-hydroxy-4-methyl-thiobutyric acid, 2-hydroxy-3-phenyl-propionic acid, starch, molasses, acetic acid, n-paraffin, glucose, etc.

The process of the present invention is able to be preferably applied for refining of histidine, serine, lysine, phenylalanine, methionine, leucine and isoleucine, particularly, leucine containing, as impurities, isoleucine, methionine, etc. which are by-products from hydrolysis of casein, keratin, hemoglobin or the like with acid, neutralization of the hydrolized compounds and purification.

The amino acid solution to be contacted with the resins having the chelate groups mentioned above should be kept at pH of about 2-12, particularly 3-10. If the pH of the amino acid solution is smaller than about 2 or greater than about 12, affinity of the desired amino acid with the chelate resin becomes lower so that efficiency of the refining is reduced.

Any method for bringing the chelate resins into contact with the amino acid solution may be used. For example, amino acid solution is passed through a column in which the chelate resins are packed, or the chelate resins are dipped in the amino acid solution and then the resins are filtered. Generally speaking, the former is preferable because an operation is easy. Preferable embodiment is that columns in which chelate resins being able to coordinate metal ions but having no metal ion coordinated are packed (hereinafter referred to as "after-column") are connected in series with columns in which the chelate resins coordinating metal ions are packed (hereinafter referred to as "previous-columns"), because contamination of the refined amino acid with the metal ions leaked from the previous-column is prevented.

Chelate resins for the previous-columns are the same as those for the after-columns. Any chelate resins may be used as long as they are able to coordinate the metal ions. Since amount of the chelate resins in the after-columns varies depending on varieties of the chelate resins and metal ions, it is usually determined by preliminary experiments. Generally, the amount is 1/1 to 1/10 to the amount of the chelate resins in the previous-columns.

Contacting temperature of the chelate reins coordinating metal ions with aqueous solution of amino acids has no special limitation, but generally it is about 0° C. to 100° C. Contacting time has no special limitation, either. The contacting tempearture and time are determined by preliminary experiments.

The process of the present invention is carried out as follows. (1) The chelate resins having chelate groups coordinating metal ions are brought into contact with the aqueous amino acid solution to be refined, in order to coordinate the amino acids on the chelate groups. In this step, other amino acids than the desired one and impurities are also adsorbed on the chelate resins. (2) The desired amino acid, other amino acids and impurities adsorbed on the chelate resins are eluted from the resins by using eluents. Then, the desired amino acid is separated from the other amino acids and impurities in accordance with a principle of chromatography in which difference in affinites to the chelate resins between the desired amino acid and the other amino acids or the impurities is used.

Eluents to be used and amount thereof vary depending on varieties of amino acids, the chelate resins, etc. They are often determined by preliminary experiments. Although known developpers for high performance liquid chromatography are employed as the eluents, preferable are water, aqueous ammonia, aqueous solution of mineral acids, caustic alkali metals, caustic alkaline earth metals, or mixtures thereof, taking into account of easiness in recovery of the amino acids. Refined amino acids are obtained from the eluate by any of conventional methods such as deposition by concentration, drying, etc.

Chelate resins from which the amino acids was removed are recycled for refining the amino acids. Alternatively, before being recycled, they are coordinated with metal ions, if necessary.

According to the present invention, amino acids of high purity are obtained very easily. Therefore, the process of the present invention is greatly economical.

In the accompanying drawings, FIGS. 1, 2, 3 and 4 represent relations between amounts of eluates and purities of amino acids in eluates in Examples 1, 2, 3 and 4, respectively.

The following nonlimiting examples further illustrate the present invention.

EXAMPLE 1

[Preparation of amino resins]

A mixture of 600 g of acrylonitrile-divinylbenzene copolymer having crosslinking degree of 6 mol %, 5150 g of diethylenetriamine and 1290 g of water, was heated up to a temperature of 115°–125° C. for 4 hours to effect an addition reaction. The resulting reaction product was filtered and washed with water to obtain 2420 g (undried) of amino resins (hereinafter referred to as amino resin (a)).

[Preparation of chelate resins]

A mixture of 242 g of amino resin (a), 144 g of acrylic acid and 36 g of water was held at a temperature of 40°–60° C. for 12 hours thereby an addition reaction was carried out. The reaction pruduct was filtered and washed with water to obtain 302 g (undried) of chelate resins having polyaminocarboxylic acid groups (hereinafter referred to as chelate resin A).

Subsequently, 30 ml of chelate resin A was brought into contact at a room temperature for 1 hour with 300 ml of aqueous solution which had been obtained by dissolving 0.1 mol of $CuSO_4$ and 0.5 mol of $NH_3$ into 1 l of water. The resulting product was filtered and washed with water to obtain chelate resin A coordinating 1.3 g of copper ions.

[Refining amino acids]

A column in which the chelate resins A coordinating copper ions were packed (a previous-column) and another column (an after-column) in which 10 ml of chelate resin A having no metal ions coordinated were packed were connected in series.

The columns were filled with deionized water. Twenty ml of aqueous solution (pH 6.2) containing 10 g/l of L-histidine and 10 g/l of L-methionine was passed through the columns for 30 minutes, and then, as the first eluent, 200 ml of deionized water was passed for 2 hours, and subsequently, as the second eluent, 200 ml of 1N aqueous ammonia was passed for 2 hours. As shown in FIG. 1, after the first eluent (deionized water) was passed, an eluate (first eluate) containing refining L-histidine was obtained and after the second eluent (aqueous ammonia) was passed, an eluate (second eluate) containing refined L-methionine was obtained.

These eluates were concentrated by evaporation under a reduced pressure. L-histidine (0.19 g) having purity of 98% and containing not more than 0.1 ppm of copper ion and L-methionine (0.18 g) having purity of 99% and containing not more than 0.1 ppm of copper ion were obtained from the first eluate and the second eluate, respectively. Yields of L-histidine and L-methionine were 93% and 90%, respectively.

EXAMPLES 2–4

The procedure of refining amino acids of Example 1 was repeated except that aqueous mixed solution of L-serine and L-leucine (Example 2), aqueous mixed solution of L-lysine and L-phenylalanine (Example 3), or aqueous mixed solution of L-isoleucine and L-leucine (Example 4) was used instead of the aqueous mixed solution of L-histidine and L-methionine. The results are shown in Table 1 and FIGS. 2–4.

TABLE 1

| Example Nos. | Amino acids | Amounts of refined amino acids (g) | Purities of refined amino acids (%) | Copper content* (ppm) |
|---|---|---|---|---|
| 2 | L-serin | 0.18 | 98 | not more than 1 |
|   | L-leucine | 0.19 | 99 | not more than 1 |
| 3 | L-lysine | 0.19 | 99 | not more than 1 |
|   | L-phenylalanine | 0.13 | 99 | not more than 1 |
| 4 | L-isoleucine | 0.19 | 99 | not more than 1 |
|   | L-leucine | 0.19 | 99 | not more than 1 |

*Contained in the refined amino acids.

COMPARATIVE EXAMPLES 1–4

The procedures for refining amino acids of Examples 1 - 4 were repeated except that chelate resin A having no metal ion coordinated was used instead of chelate resin A coordinating copper ion. After the first eluent (50 ml, deionized water) was passed the column, all of amino acids contained in the starting solutions were flowed out. Neither separation nor purification of amino acids was effected.

EXAMPLES 5–6

The procedures for refining amino acids of Examples 1 and 4 were repeated except that the after-column (in which 10 ml of chelate resin A having no metal ion coordinated was packed) was not used. The results are shown in Table 2.

TABLE 2

| Example Nos. | Amino acids | Amounts of refined amino acids (g) | Purities of refined amino acids (%) | Copper content in refined acids (ppm) |
| --- | --- | --- | --- | --- |
| 5 | L-histidine | 0.19 | 98 | 7 |
|   | L-methionine | 0.18 | 98 | 840 |
| 6 | L-isoleucine | 0.19 | 99 | 13 |
|   | L-leucine | 0.19 | 99 | 670 |

COMPARATIVE EXAMPLES 5-6

The procedures of Examples 5-6 were repeated except that the resin (1) defined below was used instead of the chelate resin A. The resin (1) was prepared by coordinating 1.2 g of copper ion with 30 ml of the amino resin (a). The results are shown in Table 3.

TABLE 3

| Comparative Examples NOs. | Amino acids | Amounts of refined amino acids (g) | Purities of refined amino acids (%) | Copper content in refined acids (%) |
| --- | --- | --- | --- | --- |
| 5 | L-histidine | 0.21 | 89 | 6.7 |
|   | L-methionine | 0.73 | 26 | 52.5 |
| 6 | L-isoleucine | 0.23 | 82 | 12.2 |
|   | L-leucine | 0.79 | 24 | 53.1 |

EXAMPLE 7

[Preparation for chelate resins]

A mixture of 242 g of the amino resin (a) prepared in Example 1, 189 g of monochloroacetic acid and 1 l of 2N aqueous solution of sodium hydroxide was heated up to 40°-50° C. for 10 hours to effect a dehydrochlorination reaction while 1N aqueous solution of sodium hydroxide was added in order to maintain pH at 8–10. The resulting reaction product was filtered and washed with water. The resin thus obtained was dipped in 500 g of 10 wt. % conc. aqueous solution of sodium hydroxide for 30 minutes at a room temperature, and then filtered and washed with water to obtain 339 g (undried) of chelate resins having polyaminocarboxylic acid groups (hereinafter referred to as chelate resin B).

Separately, aqueous solution was prepared by dissolving 0.1 mol of $CuSO_4$ and 0.5 mol of $NH_3$ in 1 l of water (hereinafter referred to as solution A). Thirty ml of chelate resin B was brought into contact with 300 ml of the solution A for 1 hour at room temperature. The resin was then filtered and washed with water to obtain chelate resin B coordinating 1.2 g of copper ion.

[Refining amino acids]

A column in which chelate resin B coordinating copper ion was packed (a previous-column) and another column (an after-column) in which 10 ml of chelate resin B having no metal ion coordinated was packed were connected in series. These columns were filled with deionized water, and 50 ml of aqueous solution of pH 3 containing 0.15 g/l of L-isoleucine, 1.5 g/l of L-leucine and 3% of NaCl was packed through the columns for 30 minutes. The L-leucine mentioned herein had 90.0% purity. And then, as the first eluent, 200 ml of deionized water was passed for 2 hours, and subsequently, as the second eluent 200 ml of 0.5N aqueous ammonia solution was passed for 2 hours. After the first eluent (deionized water) was passed, an eluate (referred to as the first eluate) containing refined L-isoleucine having purity of 99.2% was obtained, and after the second eluent (aqueous ammonia solution) was passed, an eluate (referred to as the second eluate) containing refined L-leucine having purity of 99.3% was obtained.

In this example, purity of each amino acid means as follows:

Purity of L-leucine =

$$\frac{\text{L-leucine content}}{\text{L-leucine content} + \text{L-isoleucine content}} \times 100$$

Purity of L-isoleucine =

$$\frac{\text{L-isoleucine content}}{\text{L-leucine content} + \text{L-isoleucine content}} \times 100$$

EXAMPLE 8

[Preparation for chelate resins]

A mixture of 242 g of amino resin (a) prepared in Example 1, 290 g of 25 wt. % conc. aqueous solution of formaldehyde, 164 g of phosphorous acid and 200 g of 36 wt. % conc. of hydrochloric acid was heated up to 90°-100° C. for 4 hours. The resulting reaction product was filtered and washed with water to obtain 323 g (undried) of chelate resins having diethylenetriamine methylenephosphonic acid groups (hereinafter referred to as chelate resin C).

Subsequently, 30 ml of the chelate resin C was brought into contact with 300 ml of the solution A (defined in Example 7) for 1 hour at a room temperature, and filtered and washed with water to obtain chelate resin C coordinating 0.6 g of copper ion.

[Refining of amino acids]

A column in which chelate resin C coordinating copper ion was packed (a previous-column) and an another column (an after-column) in which 10 ml of chelate resin C having no metal ion coordinated was packed were connected in series. The columns were filled with deionized water and then 100 ml of water (pH 4.7) wasted from a factories for producing methionine, containing 12 g/l of methionine, 0.6 g/l of N-methionylmethionine and 220 g/l of sodium sulfate was passed. Subsequently, 100 ml of deionized water, the first eluent, was passed for 1 hour and 200 ml of 1N aqueous triethylamine solution, the second eluent, was passed for 2 hours, in order to separate N-methionylmethionine from methionine and to refine them. Almost all of methionine in the wasted water was adsorbed on chelate resin C and contained in the eluate obtained after the second eluent had been flowed. On the other hand, almost all of N-methionylmethionine was flowed out without being adsorbed on the chelate resins in the course of passing the waste water and in the course of passing the first eluent. Purity of N-methionylmethionine in a mixture of the solution flowed out was 98%. Purity of methionine in the eluate obtained after the second eluent had been passed was 99%.

In this example, purity of each amino acid means as follows:

Purity of N-methionylmethionine =

$$\frac{\text{N-methionylmethionine content}}{\text{N-methionylmethionine content + methionine content}} \times 100$$

Purity of methionine =

$$\frac{\text{methionine content}}{\text{N-methionylmethionine content + methionine content}} \times 100$$

EXAMPLES 9–12

The procedures for refining amino acids in Example 8 were repeated except that varieties of the metal ions to be coordinated on the chelate resin C in place of Cu and their amounts were changed as shown in Table 4. The results are shown in Table 4.

TABLE 4

| Example Nos. | Metals to be coordinated and amount coordinated/ 30 ml of chelate resin C (g) | Purity of refined amino acids (%) | |
|---|---|---|---|
| | | N-methionyl-methionine in the first eluate | Methionine in the second eluate |
| 9 | $Ni^{2+}$ 0.4 | 95 | 99 |
| 10 | $Co^{2+}$ 0.6 | 91 | 98 |
| 11 | $Zn^{2+}$ 0.8 | 92 | 99 |
| 12 | $Fe^{2+}$ 1.3 | 89 | 99 |

EXAMPLES 13–21

The procedures for refining amino acids in Example 7 were repeated except that the chelate resins, D, E, F, G, H, I, J, K or l defined below were used instead of the chelate resin B.

The results are shown in Table 5.

TABLE 5

| Example Nos. | Chelate resins | Chelate groups | Amount of coordinating copper ion/30 ml of resin (g-Cu) | Purity of amino acids | |
|---|---|---|---|---|---|
| | | | | L-isoleucine in the first eluate | L-leucine in the second eluate |
| 13 | Chelate resin D | Aminocarboxylic acid | 0.9 | 67 | 98 |
| 14 | Chelate resin E | Iminodicarboxylic acid | 1.3 | 69 | 97 |
| 15 | Chelate resin F | Polyaminocarboxylic acid | 1.3 | 84 | 98 |
| 16 | Chelate resin G | Polyaminocarboxylic acid | 1.4 | 87 | 99 |
| 17 | Chelate resin H | Iminodiacetic acid | 1.3 | 67 | 98 |
| 18 | Chelate resin I | Aminophosphonic acid | 1.2 | 64 | 98 |
| 19 | Chelate resin J | Polyaminophosphonic acid | 1.3 | 99 | 99 |
| 20 | Chelate resin K | Polyaminophosphonic acid | 1.2 | 98 | 99 |
| 21 | Chelate resin L | Aminophosphonic acid | 1.2 | 65 | 98 |

Notes

Chelate resin D: Chloromethylstyrene-divinylbenzene copolymer (173 g) was allowed to react with 300 g of 20 wt. % conc. aqueous ammonia at 60° C. for 24 hours in an autoclave. The resulting reaction product was filtered and washed with water to obtain 310 g (undried) of amino resin [hereinafter referred to as amino resin (b)]. The procedure of preparation for chelate resins in Example 7 was repeated except that 310 g (undried) of the amino resin (b) was used instead of 242 g of the amino resin (a). As a result, chelate resins (390 g, undried) having aminocarboxylic acid groups were obtained. This resin was named as chelate resin D.

Chelate resin E: Into a mixed solution of 266 g of iminodiacetic acid, 80 g of NaOH and 1000 g of water, was added 173 g of chloromethylstyrene-divinylbenzene copolymer. The mixture was heated up to 60–70° C. for 24 hours. The resulting reaction product was filtered and washed with water to obtain 436 g (undried) of chelate resins having iminodicarboxylic acid groups. This resin was named as chelate resin E.

Chelate resin F: The procedure for preparation of chelate resin D was repeated except that 394 g of 80 wt. % conc. aqueous ethylenediamine solution was used instead of 300 g of the 20 wt. % conc. aqueous ammonia. As a result, 443 g (undried) of chelate resins having polyaminocarboxylic acid groups were obtained. This resin was named as chelate resin F.

Chelate resin G: The procedure for preparation of chelate resin D was repeated except that 494 g of 80 wt. % conc. aqueous diethylenetriamine solution was used instead of 300 g of the 20 wt. % conc. aqueous ammonia. As a result, 447 g (undried) of chelate resins having polyaminocarboxylic acid groups were obtained. This resin was named as chelate resin G.

Chelate resin H: This was chelate resin "Unicelex" UR-50 (trade name, manufactured by Unitika, Ltd.) having iminodicarboxylic acid groups on phenol resin.

Chelate resin I: This was chelate resin "Unicelex" UR-3300, manufactured by Unitika, Ltd.) having aminophosphoric acid groups on phenol resin.

Chelate resin J: This was chelate resin "Sumichelate" MC-76 manufactured by Sumitomo Chemical Co., having polyaminocarboxylic acid groups on acrylic resin.

Chelate resin K: This was chelate resin "Sumichelate" MC-75 manufactured by Sumitomo Chemical Co., having polyaminophosphonic acid groups on acrylic resin.

Chelate resin L: This was chelate resin "Duolite" C-467 manufactured by Duolite International Co., having aminophosphonic acid groups on polystyrene resin.

We claim:

1. A process for separating and refining a first amino acid away from at least one other amino acid, which process comprises:
   (i) contacting a chelate resin having aminocarboxylic acid groups or aminophosphonic acid groups coordinated with metal ions, with an aqueous solution containing said first amino acid and said at least one other amino acid under conditions such that said first amino acid and said at least one other amino acid are adsorbed on said chelate resin, and
   (ii) successively eluting said first amino acid and said at least one other amino acid from said chelate resin with an eluent.

2. A process according to claim 1 wherein a backbone polymer of said chelate resin is connected with said aminocarboxylic acid groups or aminophosphonic acid groups via a polyalkylene polyamino group.

3. A process according to claim 2 wherein the backbone polymer is an acrylic polymer.

4. A process according to claim 1 wherein said metal ions are transition metal ions.

5. A process according to claim 4 wherein said metal ions are selected from those belonging to the fourth period of Mendelejeff's periodic table.

6. A process according to claim 1 wherein, before step (ii), a solution resulting from step (i) is contacted with a resin capable of chelating metal ions under conditions such that coordination of metal ions present in said solution resulting from step (i) occurs.

* * * * *